United States Patent [19]

Yeoman

[11] Patent Number: 5,134,131
[45] Date of Patent: Jul. 28, 1992

[54] PHOSMET TREATMENT FOR PIG MANGE

[75] Inventor: Guy H. Yeoman, Newdigate, Nr Dorking, England

[73] Assignee: Beecham Group p.l.c., England

[21] Appl. No.: 365,239

[22] Filed: Jun. 12, 1989

Related U.S. Application Data

[63] Continuation of Ser. No. 173,427, Mar. 25, 1988, abandoned, which is a continuation of Ser. No. 867,811, May 27, 1986, abandoned, which is a continuation of Ser. No. 661,735, Oct. 17, 1984, abandoned, which is a continuation of Ser. No. 510,266, Jul. 1, 1983, abandoned.

[30] Foreign Application Priority Data

Jul. 5, 1982 [GB] United Kingdom ............... 8219377

[51] Int. Cl.$^5$ ............................................. A61K 31/675
[52] U.S. Cl. ................................................................ 514/80
[58] Field of Search ................................................ 514/80

[56] References Cited

U.S. PATENT DOCUMENTS

| | | | |
|---|---|---|---|
| 3,743,728 | 7/1973 | Fancher | 424/200 |
| 4,026,290 | 5/1977 | Brooker et al. | 128/260 |
| 4,341,760 | 7/1982 | Matthewson | 424/45 |
| 4,348,321 | 9/1982 | McDaniel et al. | 424/78 X |
| 4,395,407 | 7/1983 | Ballany et al. | 424/200 |

FOREIGN PATENT DOCUMENTS 532759 5/1980 Australia .

OTHER PUBLICATIONS

Pullar, J. Agric. Victoria, 39 (1941) pp. 99–104, 126.
Yeman, Livestock International, Part 1, Oct./Nov., 1983, pp. 116–118.
Yeman, Livestock International, Part 2, Dec. 83/Jan. 84, pp. 146–148.
Beecham Animal Health Data Sheets, Porect.
Fisons Animal Health Data Sheets, Ficare.
Animal Dermatology, Third Edition Muller et al, 1983, pp. 351–360.
J. E. Roberts et al., "Swine Control of Hog Lice on Brood Sows" Virginia Journal of Science, 31 No. 4, 1980 p. 85.
J. E. Roberts et al., "Swine Sarcoptic Mange Control", 31 No. 4 (1980) p. 85.
I. Ionova et al., Chem. Abstr. 82, 251–252, No. 2741; (1975) Full Text in Russian; Partial Translation.
R. O. Drummond, "Further Evaluation of Animal Systemic Insecticides, 1963", J. of Eco Ent. 57 No. 5 pp. 741; 745 Oct. 1964.

Primary Examiner—Frederick E. Waddell
Assistant Examiner—Kimberly R. Jordan
Attorney, Agent, or Firm—Rosenman & Colin

[57] ABSTRACT

Pig mange mite infestations are controlled or eradicated by application of a pour-on formulation containing phosmet. A suitable regime is to apply about 20 mg/kg of phosmet to sows shortly before farrowing and to boars at six monthly intervals.

5 Claims, No Drawings

PHOSMET TREATMENT FOR PIG MANGE

CROSS-REFERENCE

This is a continuation of Ser. No. 173,427 filed Mar. 25, 1988, now abandoned, which is a continuation of Ser. No. 867,811, filed May 27, 1986, now abandoned, which is a continuation of Ser. No. 661,735, filed Oct. 17, 1984, now abandoned, which is a continuation of Ser. No. 510,266, filed Jul. 1, 1983, now abandoned.

The present invention relates to a method for controlling or eradicating ectoparasites of pigs.

Phosmet (0,0-dimethyl S-phthalimidomethyl phosphorodithioate) is a known insecticide and is used for eradicating Warble Fly, an endoparasitic insect which infests cattle.

Pig mange is a particularly refractory ectoparasitic infestation of pigs caused by *Sarcoptes scabiei* var. *suis* mites. Hitherto treatment, which is normally by spraying or scrubbing the pigs, has been relatively ineffective and consequently, in the U.K., up to 35% of pigs are infested.

It has now surprisingly been found that phosmet can be used to control or eradicate ectoparasites of pigs, especially pig mange mites.

Accordingly, the present invention provides a method for controlling or eradicating ectoparasites of pigs, which method comprises applying phosmet to the ectoparasites or their environment.

The environment may, for instance, be the skin and/or ears of a pig. The ectoparasites are, especially, pig mange mites.

Alternatively, the present invention provides a method for treating or preventing ectoparasitic infestations of pigs, which method comprises topically administering phosmet to pigs.

Suitably the phosmet is applied topically to the pigs' skin and, optionally, also to their ears. Preferably the phosmet is applied to sows shortly before farrowing, e.g. from 3 to 7 days before farrowing, and to boars at approximately six-monthly intervals. Such a dosing regime restricts the transmission of ectoparasites, especially pig mange mites, between boar and sow at mating and between the sow and her piglets, and avoids the need to treat the piglets. This regime has the advantage that piglets of treated sows tend to gain weight faster than those of untreated sows and piglets of treated sows are, generally, heavier at weaning.

Accordingly the present invention also provides a method for promoting growth in piglets which method comprises administering phosmet to sows infested with ectoparasites shortly before farrowing.

Conveniently the phosmet is formulated, as a conventional pour-on formulation, in association with conventional liquid diluents or carriers. One suitable formulation is that currently marketed by Beecham Animal Health under the name αORBISECTα (registered Trade Mark), which comprises a 13.3% w/w solution of phosmet in an oily carrier. Another suitable formulation comprises a 20% w/w solution of phosmet in an oily carrier or a mixture of organic solvents.

Suitable diluents and carriers are well known to the skilled person. Preferably the formulation also contains a suitable dye to mark treated pigs and it may also contain agents to mask the odour of the solvents and phosmet, for instance up to about 1% w/w citronella is used in this way.

Suitably phosmet is applied at about 15 to 25 mg/kg, preferably about 20 mg/kg of animal body weight. When a 20.0% w/w solution of phosmet is used a suitable dosage rate is about 0.1 ml/kg of animal body weight, optionally with about 1 ml of the dose or in addition to the dose being applied in each ear flap.

The invention will now be illustrated by the following Example.

EXAMPLE 1 a) Sows, from a farm with a pig mange infestation were randomly allocated approximately three days prior to farrowing, to one of the following groups:

1) 20% phosmet medicated at a dose rate of 22 mg/kg b.w. A small part of the computed dose (1 ml) was applied inside each ear flap, 2) 2% diazinon and 1% chloroxylenol emulsifiable concentrate (Ficare, Fisons Animal Health, Loughborough) diluted 1 part in 150 of water, used as a body wash at the rate of about 2 liters per sow and, 3) untreated controls. The piglets were weighted twice, first at about 1–2 weeks after farrowing and again at weaning. Average daily liveweight gains (ADLG) were calculated. Results are given in Table 1.

b) In a further study on another farm infected sows were randomly allocated to one of the following treatment groups:

1) 20% phosmet medicated at a dose rate of 22 mg/kg body weight with 1 ml being applied inside ear flap and 2) untreated controls. The piglets were weighed at 4 weeks of age. Results are given in Table 2.

20% phosmet has been shown to exert activity against pig mange mites. Further it has been shown that by controlling the level of challenge of mange mites to piglets from the dam, that ADLG was significantly improved (Table 1). It was also found that the average piglet weight at 4 weeks was significantly higher from treated sows than from untreated controls (Table 2).

No untoward effects were seen in the pigs treated with 20% phosmet or the piglets.

TABLE 1

Effect of treatment of dams on piglet daily liveweight gain

| Sows | ADLG (g) | S.D. | No. of piglets |
|---|---|---|---|
| Group 1 | | | |
| 20% Phosmet treated | 227.0 | 59.5 | 101 |
| Group 2 | | | |
| 2% diazinon/ 1% chloroxylenol treated | 174.4 | 57.2 | 123 |
| Group 3 | | | |
| Untreated Controls | 186.6 | 51.2 | 131 |

Analysis was based on ADLG of the piglets using least significant difference between groups. ADLG was significantly greater (P 0.01) in the 20% phosmet treated group than in either the diazinon group (2) or the control group (3)

TABLE 2

Effect of treatment of dams on piglet weight at 4 weeks

| Treatment of Sows | Piglet weight | S.D. | No. of piglets |
|---|---|---|---|
| Sows treated with 20% Phosmet | 6.35 | 1.14 | 35 |
| Untreated Controls | 5.84 | 1.89 | 41 |

A covariance analysis was used, because of variation in litter size, to test the significance of the difference in average weights. This showed that the difference was significant at the 5% level and nearly so at the 1% level, the adjusted mean of the treated group being greater than that of the untreated group.

I claim:

1. A method of treating or preventing pig mange, which comprises topically applying an effective, non-toxic amount of a pour-on formulation consisting of phosmet and an oily carrier to pigs infested with pig mange mites.

2. A method according to claim 1, wherein phosmet is applied to sows before farrowing and to boars at 6-monthly intervals.

3. A method according to claim 1 wherein phosmet is applied at from 15 to 25 mg/kg.

4. A method according to claim 3 wherein phosmet is applied at about 20 mg/kg.

5. A method of treating or preventing pig mange which comprises topically applying an effective, non-toxic amount in the range of from 15 to 25 mg/kg of a pour-on formulation consisting of phosmet and an oily carrier to sows before farrowing or to boars at 6-monthly intervals.

* * * * *